US009220895B2

(12) United States Patent
Siff et al.

(10) Patent No.: US 9,220,895 B2
(45) Date of Patent: Dec. 29, 2015

(54) NONINVASIVE OR PERCUTANEOUS NERVE STIMULATION

(71) Applicants: Biowave Corporation, Norwalk, CT (US); William Beaumont Hospital, Royal Oak, MI (US)

(72) Inventors: Bradford Siff, Westport, CA (US); Kenneth M. Peters, Royal Oak, CA (US)

(73) Assignees: Biowave Corporation, Norwalk, CT (US); William Beaumont Hospital, Royal Oak, MI (US)

( * ) Notice: Subject to any disclaimer, the term of this patent is extended or adjusted under 35 U.S.C. 154(b) by 0 days.

(21) Appl. No.: 14/247,930

(22) Filed: Apr. 8, 2014

(65) Prior Publication Data
US 2014/0303682 A1    Oct. 9, 2014

Related U.S. Application Data

(60) Provisional application No. 61/809,688, filed on Apr. 8, 2013.

(51) Int. Cl.
| A61N 1/00 | (2006.01) |
| A61N 1/36 | (2006.01) |
| A61N 1/04 | (2006.01) |
| A61N 1/05 | (2006.01) |

(52) U.S. Cl.
CPC .......... *A61N 1/36021* (2013.01); *A61N 1/0456* (2013.01); *A61N 1/36007* (2013.01); *A61N 1/36014* (2013.01); *A61N 1/0502* (2013.01); *A61N 1/36003* (2013.01); *A61N 1/36017* (2013.01)

(58) Field of Classification Search
CPC .................................................. A61N 1/36007
USPC ................................................ 607/41, 46, 48
See application file for complete search history.

(56) References Cited

U.S. PATENT DOCUMENTS

| 5,069,211 | A | * | 12/1991 | Bartelt et al. ................... 607/74 |
| 6,584,358 | B2 | | 6/2003 | Carter et al. |
| 6,760,627 | B2 | | 7/2004 | Carter et al. |
| 6,792,315 | B2 | | 9/2004 | Carter et al. |
| 6,853,863 | B2 | | 2/2005 | Carter et al. |
| 7,013,179 | B2 | | 3/2006 | Carter et al. |
| 7,130,696 | B2 | | 10/2006 | Carter et al. |
| 2001/0025192 | A1 | | 9/2001 | Gerber et al. |

(Continued)

OTHER PUBLICATIONS

Uroplasty, "Urgent PC, Remarkable Results, Reduced Risk", http://www.uroplasty.com/patients/urgentpc, 4 pp., 2014.

(Continued)

*Primary Examiner* — Christopher D Koharski
*Assistant Examiner* — Nadia A Mahmood
(74) *Attorney, Agent, or Firm* — Schiff Hardin LLP (57) ABSTRACT

A system and method of stimulating a nerve of a patient is provided. A electro-therapy device is used that includes a signal generator and two electrodes. The first electrode is positioned on an epidermis of the patient over the nerve to be stimulated. The second electrode is positioned on an epidermis of the patient at a second location. A The electro-therapy device is configured to alternately deliver to a first and second electrode a summation of first and second signals which result in a therapeutic signal encompassing the nerve of the patient. The intensity of the first and second signal is adjusted over time.

20 Claims, 3 Drawing Sheets

(56) References Cited

U.S. PATENT DOCUMENTS

| | | |
|---|---|---|
| 2001/0031999 A1 | 10/2001 | Carter et al. |
| 2002/0055761 A1* | 5/2002 | Mann et al. .................... 607/41 |
| 2003/0017193 A1 | 1/2003 | Chou |
| 2003/0195590 A1 | 10/2003 | Carter et al. |
| 2008/0033492 A1* | 2/2008 | Siff et al. .......................... 607/3 |
| 2012/0036451 A1 | 2/2012 | Wang et al. |
| 2013/0006322 A1 | 1/2013 | Tai |

OTHER PUBLICATIONS

International Search Report dated Sep. 23, 2014 for International Application No. PCT/US2014/033347.

* cited by examiner

NONINVASIVE OR PERCUTANEOUS NERVE STIMULATION

RELATED APPLICATION

The present application claims priority of provisional patent application No. 61/809,688 filed Apr. 8, 2013, the contents of which are incorporated herein in their entirety.

BACKGROUND

Electro-therapy is the application of electrical energy to the body of a human patient to provide a therapeutic effect. The therapeutic effects produced by electro-therapy include the blockage of pain, residual pain relief possibly due to the release of endorphins or other opiate-like analogs, relief from headache pain, increase of blood flow, increases in the range of motion, cartilage regrowth or regeneration, accelerated bone growth, electronic epidural for childbirth and other beneficial effects that result from the introduction of a low frequency electric field into tissue beneath the skin. Electro-therapy as defined by this application does not include electro-osmosis, electroporation, or iontophoresis, or any other process in which electrical energy such as an electrical field or electric currents are used to promote the transdermal transportation of chemicals or fluids into or out of the body. Nor does it include electrosurgery where radiofrequency electrical energy is used to cut or cauterize tissue.

Electro-therapy typically includes a non-invasive technique to introduce the electrical energy into the patient's body. Disposable electrodes are placed on the epidermal surface of a patient and coupled to an electric generator. The generator supplies two or more oscillating or complex morphology electric currents to a patient, with respective selected electrodes separated from one another on the patient's body with a pain site located directly underneath at least one electrode with the majority of the electric field positioned in a hemisphere beneath the skin surface on which each electrode resides. The electric currents have frequencies of at least about 1 KHz and differing by as little as 1 Hz up to about 250 Hz from each other. A nonlinear action of nerve fiber membranes and/or other electrochemically-active structures or fluids causes a multiplication of the two independent frequency signals in a volume of tissue surrounding and beneath each electrode to produce a therapeutic effect in depth. The mixing yields a distribution of synthesized sum and difference frequencies among which is a therapeutic low frequency equivalent to a beat frequency of the signals.

In order to penetrate the tissue beneath the skin and provide a therapeutic effect, electrical signals applied to the body must overcome the electrical impedance of the skin. Electrical impedance is a property of the skin that limits the amount of current that can pass through the skin. The top layer of the skin, the stratum corneum, is made up of dead skin cells and contributes to the skin's high electrical impedance. Dry, intact skin can have an impedance which exceeds a hundred thousand ohms. Even carefully prepared skin, i.e., where the hair has been shaved or otherwise removed, where debridement of devitalized or contaminated tissue has been performed, and where the skin's surface has been moisturized, can still have an impedance of over one thousand ohms. A potentially large voltage would be necessary to overcome the skin impedance and drive a therapeutically useful amount of electrical current at a frequency through body tissues, but the large voltage and resulting high current density may cause a significant burn at the surface of the skin. The relatively large amount of energy required, limits the voltage level that can be applied as well as the amount of time that a portable generator device powered by batteries can be used.

It is known in the art that applying electrical energy to the skin can reduce the impedance of the skin. For example, Carim et al. discloses in their U.S. Pat. No. 6,032,060 issued on Feb. 29, 2000 directing electrical energy through a medical electrode placed on the skin of the patient in order to electrically condition the skin. The reduction in skin impedance increases the ability to monitor bioelectric signals and can reduce the amount of energy necessary for electroporation or transdermal iontophoresis.

Known devices and systems are designed for sensing electrical signals generated by the body or for delivering pharmaceuticals to the body. These devices have physical characteristics and electrical properties that make them suitable for their intended uses. Thus, while methods and systems to penetrate beneath the skin to provide a therapeutic effect are known, they are generally invasive and difficult to administer. What is needed is a non or minimally invasive method and system of stimulating a nerve for a therapeutic effect, particularly methods and systems that are compatible with a Biowave® stimulator and electrodes.

DETAILED DESCRIPTION

The present disclosure generally relates to methods and systems of an electro-therapy and more particularly to a method and system for applying a therapeutic electrical signal for stimulating a nerve. The method and system described herein uses Biowave® technology, including a Biowave® stimulator and Biowave® electrodes (e.g., noninvasive and/or percutaneous). The Biowave® array of needles in the percutaneous electrode provides a direct conductive pathway through the outer layers of skin resulting in an efficient manner for delivering therapeutic electrical energy into the body of a patient, which is provided by an electro-therapy generator device. An electro-therapy generator device suitable for the production of such energy is described in U.S. Pat. No. 6,584,358, entitled "Electro-Therapy Method and Apparatus," to Carter et al., assigned to Biowave® Corporation, which is hereby incorporated by reference in its entirety for each of its teachings and embodiments.

Figure 1A:
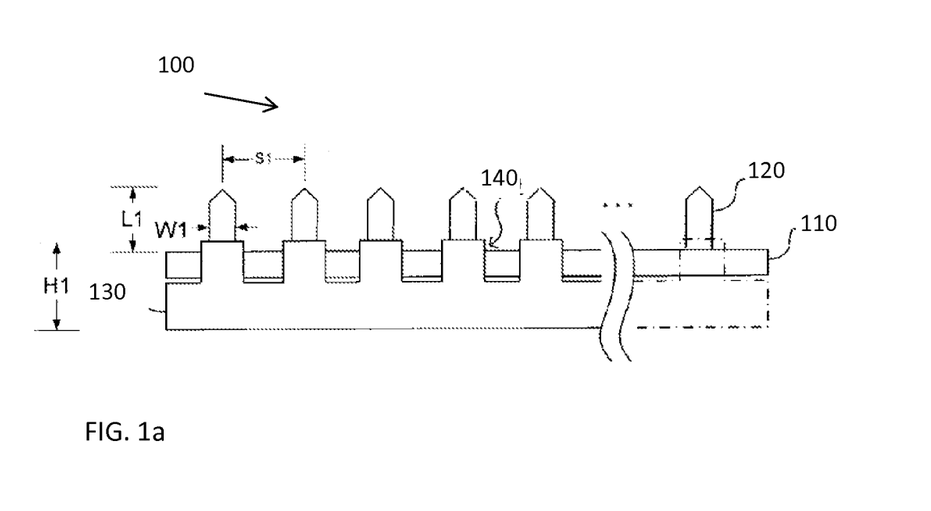
FIG. 1a illustrates a top view of an exemplary percutaneous electrode array for applying therapeutic electrical energy to a treatment site in the body of a patient.
Figure 1B:
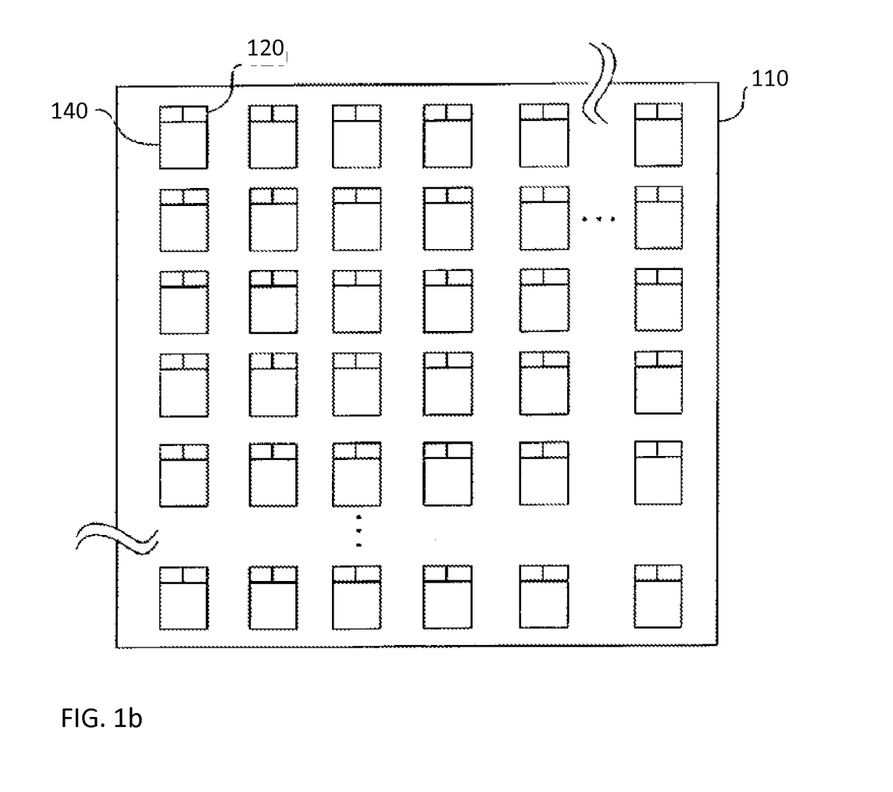
FIG. 1b illustrates a side view of an exemplary percutaneous electrode array for applying therapeutic electrical energy to a treatment site in the body of a patient.

Exemplary Biowave® electrodes that are suitable for overcoming the electrical impedance of the skin are described in U.S. Pat. No. 6,792,315 to Carter et al., entitled "Electro Therapy Method and Apparatus," and U.S. Pat. No. 7,013,179 to Carter et al. entitled "Percutaneous Electrode Array," both assigned to Biowave® Corporation, which are hereby incorporated by reference in their entirety for each of their teachings and embodiments. FIGS. 1a and 1b illustrate a top and side view, respectively, of an exemplary percutaneous electrode array for applying therapeutic electrical energy to a treatment site in the body of a patient. The percutaneous electrode 100 includes a substrate 110, a plurality of electrodes 120, an adhesion layer 130, and a plurality of voids 140 in substrate 110. Adhesion layer 130 is mounted to a rear side of substrate 110 and protrudes through voids 140 in substrate 110. Adhesion layer 130 secures the electrode to the patient, and preferably aids in the conduction of the electrical signal into the body. Substrate 110 provides support for adhesion layer 130.

Each electrode 120 may comprise a rectangular parallelepiped attached at a proximal end to the substrate. Alternatively, each electrode 120 may comprise a cylinder or cone. The distal end of either electrode embodiment preferably further comprises one or more of a rounded triangular and pointed tip. In one embodiment, the width or diameter W1 of each electrode is between 20 to 250 micrometers.

The total surface area of the electrodes in the percutaneous array equals the area of each electrode times the number of electrodes in contact with the skin. This area is large enough to carry the electrical current introduced into the body by the electro-therapy generator device, while limiting the current density through the attached skin area. The surface area of each percutaneous electrode comprises the area of the distal tip of the electrode plus the surface area along both sides of the effective length of the electrode, L1, i.e. the length that is inserted into the skin. Preferably, the total percutaneous electrode surface area is greater than 0.2 square centimeters.

In another example, the total electrode surface area is less than 0.2 square centimeters, but the substrate has a surface area greater than 14.1 square millimeters. The current conducting area of the substrate in combination with the area of the electrodes limits the current density to the skin.

The effective contact area of the electrodes is equal to the total surface area of the electrodes times a reduction factor (e.g., 56%) that accounts for the electrode element surface area which comes in contact with the body's ionic environment (e.g., 70% of the electrode's length), and the number of electrodes that are in contact with the skin (e.g., 80% of the total number of electrodes in the array). The Food and Drug Administration (FDA) currently limits the current density for electro-therapy devices to less than 10 milliamps per square centimeter of contact area. Several different configurations can be used in order to achieve the effective contact area to reduce the current density below the FDA limit. One way to increase the area is to increase the length L1 of each electrode 120 in the percutaneous electrode array, i.e., the length in contact with the ionic environment of the body, in order to maximize the area for electrical conduction. The maximum length is determined by observing the structure of the skin in the human body.

The Biowave® stimulator is an electro-therapy generator device. The stimulator can be configured to produce a summation of high frequency alternating current signals that are delivered into a single electrode. For example the stimulator provides a summation of two alternating current sine waves such that the body produces the desired internal electrical field at a specific frequency that will achieve optimal nerve stimulation. In one embodiment, the delivery of a summation of the first and second signals to the first electrode and the second electrode is alternated. The high frequency signals are able to pass through skin into deeper tissues. A therapeutic electrical field encompassing the nerve of the patient in a volume of tissue surrounding and beneath each respective first and second electrode is formed. In a hemisphere beneath the electrode, polarized structures including the membrane of nerves act in a nonlinear manner and facilitate the multiplication of the two high frequency signals resulting in a new spectrum of signals. The spectrum includes a low frequency signal in the form of an electrical field that has the ability to stimulate a nerve fiber. The multiplication of two alternating current high frequency signals can be performed via Fourier transform. The multiplication effect occurs inside the body, which was proven in a rabbit model.

In one implementation, the two high frequency electronic signals referred to herein as "Feed Signals" are provided into the body non-invasively through a first Biowave® electrode placed on the epidermis at a predetermined location (e.g., directly over the location of the nerve to be stimulated). The Feed Signals are multiplied together by materials within the body giving rise to a low frequency component (i.e., the beat frequency) in the form of an electric field that develops in a hemisphere surrounding and beneath the first electrode. The size of the volume of tissue affected can be changed and is dependent upon the amplitude of the Feed Signals, electrode placement, geometry and materials. The Feed Signals then continue to pass through the body to a second Biowave® electrode and return to the Biowave stimulator to complete the circuit. The Biowave® stimulator then delivers the Feed Signals into the body non-invasively directly through the second Biowave® electrode, which is placed on the epidermis over a second location beneath which a nerve is to be stimulated, or over a bony prominence that is a comfortable location to receive the stimulation. The actual location of the first electrode and second electrode (which are disposable in this example) depends on the therapeutic effect desired and will be discussed in more detail in a later section.

The two electrodes are positioned on predetermined locations on the patient's body. The first electrode is positioned directly on the epidermis over the nerve to be stimulated. The second electrode is positioned on a second portion of the patient's body based on the targeted nerve(s). In one embodiment, the ratio of the area of the second pad to the area of the first electrode is 1:1. In another embodiment, the ratio of the area of the second electrode to the area of the first electrode is at least 2:1. The electrode size ratio depends upon the application, the number of nerves to be stimulated, the number of locations along one nerve that require stimulation as well as the location of the electrodes (e.g., pads) on the body, which will be discussed more in a later section.

The application of physiologically high frequency Feed Signals (e.g., 1 kHz-100 kHz), alternately introduced through independent electrodes gives rise to a spectrum of frequencies as a consequence of the nonlinear operations performed by polarized structures, for example nerve membranes that lie within the volume of tissue around and beneath each electrode (i.e., the treatment site(s)). This nonlinear operation yields both sum and difference frequencies from the two original Feed Signals. One of the frequencies generated (i.e., the difference between the Feed Signals) is called the Beat Frequency and is within the range (1 Hz-250 Hz) that has been determined to have a therapeutic effect for the particular application.

Stimulation of different nerve fibers can produce beneficial treatment results for several different types of afflictions. For example, some clinical trials have indicated that implanted stimulation devices or the implantation of a needle down to the nerve for its stimulation can produce beneficial outcomes. In this regard, stimulation of the sacral nerve can reduce pelvic floor pain. Stimulation of the tibial nerve reduces the symptoms affiliated with over active bladder syndrome and incontinence (e.g., urinary and/or fecal). Stimulation of C-fiber and A-delta fibers can reduce the transmission of pain signals, improve range of motion and reduce stiffness, and stimulation of muscle tissue may decrease muscle spasm.

Where previous devices generally required implantation of a needle deep in the location of the nerve or even an entire electronic device, lead wire, and electrode implanted in the body, the Biowave® technology and methods discussed herein effectively stimulate nerves to achieve a therapeutic benefit. For example the therapeutic benefit may be to reduce pain and/or cure over active bladder syndrome and/or incontinence noninvasively with Biowave® electrodes (i.e., a surface electrode and/or a percutaneous electrode comprised of an array of 316L surgical grade stainless steel microneedles. This enables treatment of the foregoing symptoms with a small comfortable hand held Biowave® electro-therapy generator device that may be operated by a patient in a clinic setting, at home, etc., and thus without doctor supervision.

Figure 2:
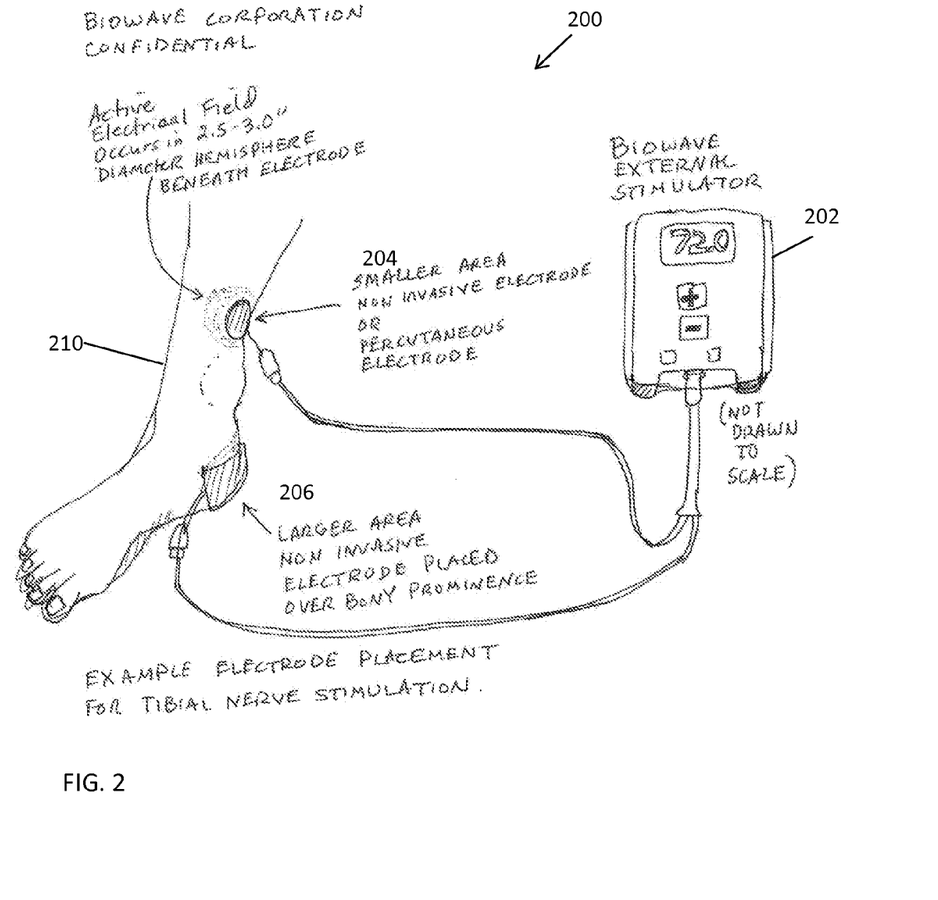
FIG. 2 illustrates an exemplary system for nerve stimulation of an exemplary embodiment.

FIG. 2 illustrates an exemplary system for nerve stimulation, consistent with an exemplary embodiment. System 200 includes an external Biowave® stimulator 202 configured to provide therapeutic electrical energy to a patient 210. The Biowave® stimulator 202 includes electrical circuitry configured to produce first and second Feed Signals, which allows the body to create a therapeutic signal from the first and second Feed Signals. The system includes a first electrode 204 and a second electrode 206, both coupled to the Biowave® stimulator 202. Both the first and second Feed Signals are alternately applied to the patient 210 through the first electrode 204 and then through the second electrode 206 respectively to form the therapeutic signal inside the body. The therapeutic signal that is developed inside the body beneath both the first and second electrodes 204, 206 can be regulated in amplitude and frequency to produce the desired effect. The voltage of the signal applied via the electrodes can be regulated from 0 Volts to a maximum voltage via the Biowave® electro therapy generator device 202. In one embodiment, the maximum voltage is set to 27.5 Volts.

In one embodiment, the first electrode 204 and the second electrode 206 each comprise a single pad, wherein the second electrode 206 is larger than the first electrode 204. Each electrode may be a Biowave® noninvasive electrode or a minimally invasive percutaneous electrode. In one embodiment, one of the electrodes is a Biowave® non-invasive electrode while the other electrode is a Biowave® percutaneous electrode.

While FIG. 2 illustrates a foot that is used for tibial nerve stimulation, it will be understood that the electrodes can be applied to different parts of the body depending on the nerve(s) to be stimulated and the therapeutic results desired, as will be made clearer with the various examples below.

As discussed above the Biowave® electrodes 204 and 206 may be both noninvasive, both percutaneous, or any combination thereof. The electro therapy generator device e.g., Biowave® stimulator) 202 provides optimal delivery of the Biowave® signals through the epidermis of a patient directly above the nerve to be stimulated. The size of the Biowave® electrodes used is based on the targeted nerve(s) in question. Four different combinations of Biowave® electrodes are discussed below.

In a first exemplary combination, both the first and second electrodes 204 and 206 are non-invasive. Further, both electrodes 204 and 206 are of equal area such that the density of the electrical field will be the same under each electrode. The active electrical field forms in an equal hemisphere beneath each electrode 204, 206. The diameter of the hemisphere of the active electrical field is slightly larger than the diameter of the electrode.

Figure 3A:
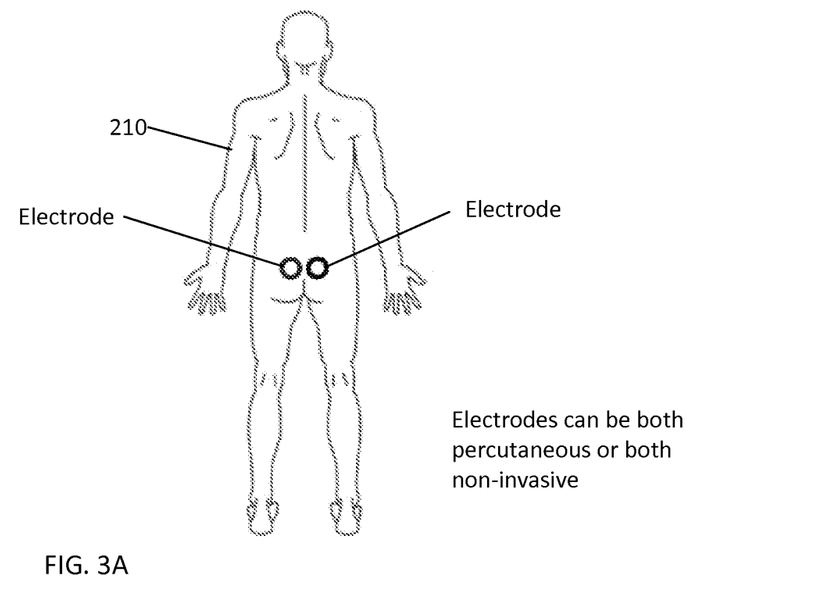
FIG. 3A illustrates an exemplary placement of electrodes for bilateral sacral nerve stimulation.
Figure 3B:
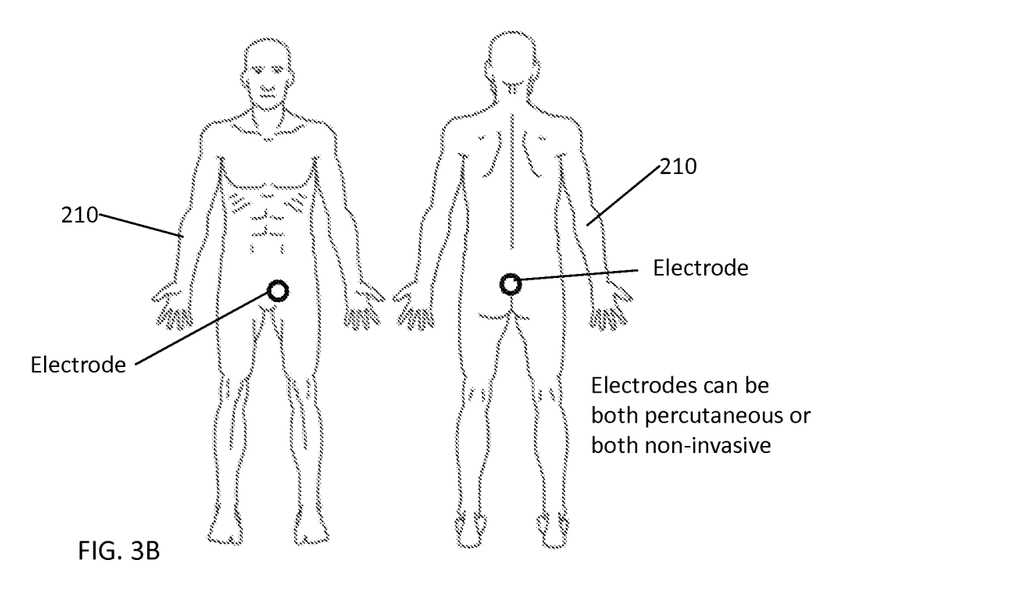
FIG. 3B illustrates an exemplary anterior and posterior placement of electrodes for sacral nerve stimulation.

The first exemplary combination provides an equal treatment on two separate nerves, which can be in two different locations. In this regard, FIG. 3B illustrates an exemplary anterior and posterior placement of electrodes for sacral nerve stimulation. Alternatively, the two electrodes are placed adjacent and within a predetermined radius (e.g., distance) of each other to treat multiple branches of a nerve or one nerve over a larger area. In this regard, FIG. 3A illustrates an exemplary placement of electrodes for bilateral sacral nerve stimulation. This is one of two preferred placements for sacral nerve stimulation treatment. In one example, one electrode can be positioned over the pubis on the anterior of the body, and one electrode can be positioned centrally over the sacrum on the posterior of the body, as illustrated in FIG. 3B. In another example, two same size electrodes can be placed bilaterally over the sacrum, capturing the left and right branches of the sacral nerve, as illustrated in FIG. 3A. The minimum distance between the two electrodes is one inch for bilateral sacral nerve stimulation. In one example, to treat a single nerve over a larger area, two electrodes of the same size can be positioned one inch apart from one another—both located directly over the nerve pathway in the body. For example, the nerve stimulation of this exemplary combination can be performed at home (e.g., by the patient without doctor supervision).

In a second exemplary combination, both the first and second electrodes 204 and 206 are non-invasive. The external stimulator 202 alternates the delivery of an equal voltage to the first and second electrodes. The first (e.g., primary) electrode has a surface area that is smaller than the second electrode. Put differently, the second electrode is larger in area than the first electrode 204. The density of the electrical field (and thus the sensation to the patient 210) is greater under the first (i.e., smaller area) electrode 204. This first electrode 204 is positioned directly on the epidermis over the nerve to be stimulated. The active electrical field forms in a hemisphere beneath the first electrode 204. The diameter of the hemisphere of the active electrical field is slightly larger than the diameter of the first electrode 204. While the density (and therefore the sensation to the patient 210) from the electrical field is much less under the second (i.e., larger area) electrode 206. Depending on the type of tissue beneath the second electrode (nerves, muscle, bony prominence, etc.,) the patient may perceive the sensation from the second electrode to be anywhere from 0% to 80% of the sensation felt under the smaller first electrode. The least sensation is perceived by a patient when the larger second electrode is placed over a bony prominence. The second electrode 206 is also placed within a predetermined radius with respect to the nerve to be stimulated. In one embodiment, the minimum distance between the first and second electrodes is 0.5 inches, while there is no limitation for a maximum distance. For example, the second electrode is placed near the region where the first electrode 204 is positioned. The second larger electrode provides some therapeutic benefit in the hemisphere beneath it but significantly less than the benefit derived in the hemisphere beneath the smaller electrode. Placing the second electrode over a bony prominence in a region near the first electrode allows a greater active electrical field in total to be delivered into the desired volume of tissue (i.e., the active electrical field is being created beneath both the first and second electrodes). In one embodiment being in the proximity of the first electrode 204 is not required. For example, to stimulate the ulnar nerve, a smaller first electrode can be placed on the medial side of the elbow directly over the ulnar nerve. The comfortable bony prominence location for the larger rectangular second electrode is not in nearby proximity on the elbow rather on the shoulder; one corner of the larger rectangular second electrode is placed over the acromioclavicular joint and the body of the rectangular electrode is positioned at an angle across the spine of scapula on the posterior of the shoulder. Stimulation over a bony prominence is the most comfortable place to receive the Biowave® stimulation. In this regard, a patient 210 can receive a higher intensity nerve stimulation (e.g., via a higher setting on the external stimulator 202). Accordingly, a more dense electrical field forms under the first (smaller) electrode 204 encompassing the targeted nerve.

The higher the intensity (e.g., voltage applied to the stimulated nerve by the stimulator 202 via the electrodes 204 and 206), the greater the efficacy and the longer the residual effect of the therapeutic treatment. The intensity of the therapeutic signal from the stimulator may change over time. In one embodiment, the patient 210 is allowed to adjust the intensity of the therapeutic signal to achieve the highest intensity while still being comfortable. In various embodiments, the patient 210 may be allowed to adjust the intensity during predetermined intervals or during the entire electrical nerve stimulation session. In one example, the regulation of intensity for tibial nerve stimulation includes increasing the intensity to tolerance during the first interval (e.g., 5 minutes) of the treatment and then keeping the intensity constant for the remainder of the treatment (e.g., 30 min).

Of course, if the second electrode 206 is positioned in a location that is comfortable to the patient 210, the patient 210 may increase the intensity of the stimulation to a higher level. Thus, in one embodiment, the intensity of the first and second signal applied by the external stimulator 202 that the patient may tolerate (e.g., manually adjust) is only limited by the strength of the sensation under the first electrode 204. That is because the second electrode 206 is placed at an inherently comfortable position (e.g., bony prominence). The foregoing second exemplary combination is the preferred placement for a tibial nerve stimulation treatment that may be performed at home (e.g., by the patient without doctor supervision).

In a third exemplary combination, both the first and second electrodes 204 and 206 are percutaneous and of substantially similar size. In a preferred embodiment, the sterile percutaneous electrodes from Biowave® are used for best results. Thus, the first electrode has a surface area and shape that is substantially similar to that of the second electrode. As discussed above, percutaneous electrodes each have an array of microneedles that are configured to be inserted into the epidermis of a patient 210. Percutaneous electrodes overcome the inherent electrical impedance of the outer skin layers (epidermis). The microneedle array of an electrode may include a conductive adhesion layer to help keep the microneedles inserted into the epidermis during the duration of the treatment. In one embodiment, the percutaneous electrode array has approximately 1000 microneedles, 0.75 mm in length centered within a 2.5" diameter patch that contains a hydrogel base layer.

Since the area of the microneedle array is substantially similar for both the first and second electrodes 204, 206, both electrodes provide an equally direct pathway for delivering the therapeutic electrical signal through the epidermis into deeper tissue of the patient 210 by bypassing the impedance and capacitance of the skin. The low impedance connection of the first electrode 204 and the second electrode 206 is substantially similar in this third exemplary combination. Additionally, since the surface area of the electrodes is the same, the density of the electrical field will be the same under each electrode 204, 206. The active electric field forms in an equal diameter hemisphere beneath each electrode 204, 206. The diameter of the hemisphere of the active electrical field is slightly larger than the diameter of the electrode.

The foregoing third exemplary combination can provide an equal treatment on two separate nerves, which can be in two different locations. Alternatively, the two electrodes are placed adjacent and within a predetermined radius to each other to treat one nerve over a larger area or multiple branches of the same nerve. This is the second of two preferred placements for sacral nerve stimulation treatment. In one example, this sacral nerve stimulation can be performed at home (e.g., by the patient without doctor supervision).

In a fourth exemplary combination, the first electrode 204 is a Biowave® percutaneous electrode, while the second electrode 206 is a Biowave® non-invasive electrode. The external stimulator 202 alternates the delivery of an equal voltage to the first and second electrodes. The first (e.g., primary) electrode 204 has a surface area that is smaller than that of the second electrode 206. Put differently, the second electrode is larger than the first electrode 204. The density of the electrical field (and thus the sensation to the patient 210) is greater under the first (i.e., smaller area) electrode 204 both because of the smaller size and because of the smaller impedance. Thus, the first electrode has an impedance that is significantly less than the impedance of the second electrode. The first (percutaneous) electrode 204 is positioned directly over the nerve to be stimulated. The active electrical field forms in a hemisphere beneath the first electrode 204. The diameter of the hemisphere of the active electrical field (of the first electrode 204) is slightly larger than the diameter of the first electrode 204. While the density and the sensation from the electrical field is less under the second (i.e., noninvasive and larger area) electrode 206, the second electrode 206 is still placed over a bony prominence typically near the region (e.g., predetermined radius) where the first electrode 204 is positioned. In one embodiment being in the proximity of the first electrode 204 is not required.

As discussed in the context of the second exemplary combination above, stimulation over a bony prominence is the most comfortable place to receive the Biowave® stimulation. In this regard, a patient 210 can receive a higher intensity nerve stimulation (e.g., via a higher setting on the external stimulator 202). Accordingly, a more dense electrical field forms under the first (smaller and percutaneous) electrode 204 over the targeted nerve.

The higher the intensity (e.g., voltage applied to the stimulated nerve by the stimulator 202 via the electrodes 204 and 206), the greater the efficacy and the longer the residual effect of the therapeutic treatment for certain nerve stimulation applications, such as pain nerves. The intensity of the therapeutic signal from the stimulator may change over time. In one embodiment, the patient 210 is allowed to adjust the intensity of the therapeutic signal to achieve the highest intensity while still being comfortable. Higher intensity stimulation can provide better treatment outcomes to the extent it is comfortable and well tolerated by the patient 210. For example, over-stimulation may result in fatigued muscle tissue and the patient 210 may be sore post treatment. In various embodiments, the patient 210 may be allowed to adjust the intensity during predetermined intervals or during the entire electrical nerve stimulation session. The foregoing fourth exemplary combination may be used to stimulate a tibial nerve in a therapy session. In one embodiment, the session is performed in a medical office setting. For example, the tibial nerve may be stimulated to treat patients with overactive bladder symptoms of urinary urgency (OAB) and incontinence.

It should be noted that the four exemplary combinations discussed above may be used for stimulating C and A nerve fibers for the treatment of pain. It will be understood that the placement of the first and second electrodes 204, 206 will vary based on the location and type of pain.

The first (e.g., Biowave®) electrode 204 is generally positioned directly on the epidermis over the nerve to be stimulated. The location of the second (e.g., Biowave®) electrode 206 depends on the nature of the treatment. The second (e.g., Biowave®) electrode 206 is placed over one of the following: (1) a second nerve to be stimulated; (2) over the source of the pain (which may be different from the location that the pain presents); (3) over an adjacent location over the primary nerve to be stimulated; or (4) over a bony prominence (a comfortable location to receive stimulation) near the region being treated.

In one embodiment, the intensity of the therapeutic signal from the stimulator may change over time. For example, the intensity may start at a lower level (lower voltage applied through the first and second electrodes 204 and 206) and nonlinearly increase over time. In another embodiment, the intensity increases at one or more predetermined intervals, as in a step function. The intensity slowly increases to improve stimulation while maintaining a strong but comfortable steady state sensation in each step. In one embodiment, the adjustment in intensity is in response to an interactive comfort setting by the patient 210. For example, the patient 210 may adjust the intensity of the therapy via controls of the external stimulator 202 to increase (or decrease) the intensity to a strong but comfortable level of sensation over the first time period (e.g., several minutes) of the treatment. The body of the patient 210 generally quickly adapts to the electrical field in each interval and the sensation diminishes after several seconds. As the sensation diminishes, the intensity may be increased to improve stimulation while maintaining a strong but comfortable steady state sensation. This adjustment may be performed by preprogrammed settings on the external stimulator 202 or interactively by the patient 210.

The therapy session generally lasts a predetermined period (e.g., 20 to 30 min). As discussed above, the therapy session may include different intensity steps. In one embodiment, after the first predetermined interval, the intensity of the treatment is maintained. Put differently, the first predetermined interval is used for the adjustment of the intensity to the highest intensity that is still comfortable to the patient 210 while the second predetermined interval (e.g., the remainder of the 30 minute treatment) the adjusted intensity is maintained. During the second predetermined interval, the body of the patient 210 may still adapt to the electrical field but at a much slower rate than during the first several minutes.

For example, for pain therapy applications as the sensation of the input stimulation diminishes, the intensity may start at a lower level (e.g., lower voltage applied through the first and second electrodes 204 and 206) and nonlinearly increase over time to maintain a strong but comfortable steady state sensation during the entire duration of the treatment. The intensity adjustment may be electronically controlled by the external stimulator 202 or manually by the patient 210 interacting with the external stimulator 202.

For example, for sacral nerve stimulation, the intensity of the stimulation may be continually increased to a medium sensation over the first interval (e.g., 5 minutes) of treatment. The intensity level is then maintained for the remainder (i.e., second interval) of the treatment session (e.g., 20 to 30 minutes).

For example, for tibial nerve stimulation, the intensity of the stimulation may be continually increased to a medium sensation over the first interval (e.g., 5 minutes) of the treatment or until the big toe exhibits an uncontrolled motor response. At this time, the intensity level is kept unchanged for the remainder of the treatment session (e.g., 20 to 30 minutes).

In another example, for tibial and sacral nerve stimulation applications, the intensity is only increased during a first predetermined interval (e.g., 5 min.) and then maintained constant for the remainder of the therapy session (e.g., 30 min). In one embodiment, the patient 210 performs the adjustment during the first predetermined interval.

When a countdown timer (e.g., of the Biowave® stimulator) reaches zero minutes and seconds, the intensity of the first and second electrodes automatically drops to zero and the therapeutic treatment stops. In one embodiment, the patient 210 can halt the application of the first and second signals after a predetermined time (e.g., 5 minutes of therapy).

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings. Accordingly, the disclosure is intended to cover alternatives, modifications and equivalents, which may be included within the scope of the disclosure.

While the foregoing has been described in conjunction with exemplary embodiments, it is understood that the term "exemplary" is merely meant as an example, rather than the best or optimal.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. A method of stimulating a nerve of a patient, comprising:
   providing an electro-therapy device comprising:
      a signal generator configured to produce first and second signals; and
      a first and a second electrode;
   positioning the first electrode on an epidermis of the patient over the nerve to be stimulated;
   positioning the second electrode on an epidermis of the patient at a second location;
   alternating the delivery of a summation of the first and second signals to the first electrode and the second electrode, wherein the first and second signals penetrate through the epidermis into deeper tissue;
   forming, from the first and second signals, a therapeutic electrical field in the deeper tissue encompassing the nerve of the patient within a volume of tissue surrounding and beneath each respective first and second electrode; and
   adjusting an intensity of the first and second signal over time.

2. The method of claim 1, wherein the adjustment of the intensity of the first and second signal slowly increases to improve stimulation.

3. The method of claim 2, wherein the adjustment of the intensity is in response to an interactive comfort setting by the patient.

4. The method of claim 1, further comprising halting the application of the first and second signals after a predetermined time.

5. The method of claim 4, wherein the predetermined time is 20 to 30 minutes.

6. The method of claim 1, wherein the second location is on an epidermis of the patient at one of:
   (1) over a second nerve to be stimulated;
   (2) over a source of a pain;
   (3) within a predetermined radius of the nerve to be stimulated; or
   (4) over a bony prominence within a predetermined radius with respect to the nerve to be stimulated.

7. The method of claim 1, wherein:
   the nerve is a sacral nerve;
   the first and second electrodes are non-invasive electrodes;
   the first and second electrodes are of equal area such that the density of the electrical field is the same under the first and second electrodes; and
   an active electrical field forms in an equal hemisphere beneath each electrode.

8. The method of claim 7, wherein a diameter of the hemisphere is larger than a diameter of each electrode.

9. The method of claim 7, wherein the first and second electrodes are placed adjacent and within a predetermined radius of each other to treat multiple branches of the nerve.

10. The method of claim 7, wherein the nerve stimulation is performed by the patient without a doctor supervision and part of a therapy to at least one of (i) reduce pelvic floor pain, and (ii) improve range of motion of the patient.

11. The method of claim 1, wherein:
   the nerve is a tibial nerve;
   the first and second electrodes are non-invasive electrodes and are configured to each create an electrical field in a body of the patient;
   the first electrode has a surface area that is smaller than a surface area of the second electrode such that the density of the electrical field is greater under the first electrode than the second electrode; and
   a diameter of a hemisphere of an active electrical field beneath the first electrode is larger than a diameter of the first electrode.

12. The method of claim 11, wherein the second electrode is positioned over a bony prominence on a body of the patient.

13. The method of claim 12, wherein the second electrode is positioned within a predefined radius of the nerve.

14. The method of claim 12, wherein the nerve stimulation is performed by the patient without a doctor supervision and is part of a therapy to cure symptoms of urinary or fecal incontinence and overactive bladder syndrome (OAB).

15. The method of claim 11, wherein the nerve stimulation is performed by the patient without a doctor supervision and is part of a therapy to cure symptoms of urinary or fecal incontinence and overactive bladder syndrome (OAB).

16. The method of claim 1, wherein:
   the nerve is a sacral nerve;
   the first and second electrodes are percutaneous electrodes and are configured to each create an electrical field in a body of the patient;
   the first and second electrodes are of substantially similar surface area and shape;
   a diameter of a hemisphere of an active electrical field beneath the first electrode is substantially similar to an active electrical field beneath the second electrode; and
   the diameter of the hemisphere of each active electrical field is slightly larger than the diameter of each electrode.

17. The method of claim 16, further comprising positioning the second electrode on a second sacral nerve of the patient.

18. The method of claim 1, wherein:
   the nerve is a tibial nerve;
   the first electrode is a percutaneous electrode and the second electrode is a non-invasive electrode, the electrodes being configured to each create an electrical field in a body of the patient;
   the first electrode has an impedance that is less than the impedance of the second electrode;
   a diameter of a hemisphere of an active electrical field beneath the first electrode is larger than an active electrical field beneath the second electrode; and
   the diameter of the hemisphere of each active electrical field is slightly larger than the diameter of each electrode.

19. The method of claim 18, wherein the second electrode is positioned over a bony prominence on a body of the patient.

20. The method of claim 18, wherein the second electrode is positioned within a predefined radius of the position of the first electrode.

* * * * *